United States Patent [19]
Williams et al.

[11] Patent Number: 6,020,524
[45] Date of Patent: Feb. 1, 2000

[54] PROCESS FOR THE PREPARATION OF 2-(PYRID-2-YLOXYMETHYL) PHENYLACETATES AS PESTICIDE INTERMEDIATES

[75] Inventors: Alfred Glyn Williams, Binfield; Gordon Richard Munns, Reading; Paul Anthony Worthington, Maidenhead, all of United Kingdom

[73] Assignee: ZENECA Limited, United Kingdom

[21] Appl. No.: 09/277,911

[22] Filed: Mar. 29, 1999

Related U.S. Application Data

[62] Division of application No. 09/029,026, filed as application No. PCT/GB96/02337, Sep. 24, 1996, Pat. No. 5,942,623.

[30] Foreign Application Priority Data

May 10, 1995 [GB] United Kingdom ............... 9520355

[51] Int. Cl.$^7$ ..................... C07D 213/55; C07C 57/32
[52] U.S. Cl. ............................. 562/496; 546/303
[58] Field of Search ............... 562/496; 546/303

[56] References Cited

U.S. PATENT DOCUMENTS 4,045,438  8/1977  Haviv et al. ................... 544/29
4,128,572  12/1978  Cassar et al. ................. 562/406

OTHER PUBLICATIONS

Chemical Abstracts, vol. 121, 83940, 1994.
Chemical Abstracts, vol. 117, 192087, 1992.
Chemical Abstracts, vol. 115, 136720, 1991.
Chemical Abstracts, vol. 112, 235795, 1990.
Chemical Abstracts, vol. 99, 175202, 1983.
Chemical Abstracts, vol. 92, 147010, 1980.
Chemical Abstracts, vol. 88, 6363, 1978.

*Primary Examiner*—Alan L. Rotman
*Attorney, Agent, or Firm*—David P. LeCroy

[57] ABSTRACT

A compound of the following formula

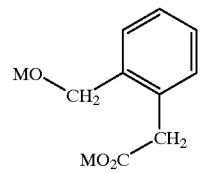

(III)

wherein M is an alkali metal or alkaline earth metal atom and a process for the preparation of the compound is provided.

3 Claims, No Drawings

PROCESS FOR THE PREPARATION OF 2-(PYRID-2-YLOXYMETHYL) PHENYLACETATES AS PESTICIDE INTERMEDIATES

CROSS-REFERENCE

This application is a Div. of application Ser. No. 09/029,026 filed Feb. 19, 1998, now U.S. Pat. No. 5,942,623, which is a 371 of PCT/GB96/02337 filed Sep. 24, 1996.

The present invention relates to a chemical process and, more particularly, to a process for preparing 2-(pyrid-2-yloxymethyl)phenylacetates. These compounds are useful as intermediates for producing agricultural pesticides.

Some new agricultural fungicides and insecticides, which are methyl 2-[2-(aryl- and heteroaryloxymethyl)phenyl]-3-methoxyacrylates, are described in EP-A0278595 along with a variety of methods for their preparation. In one method described, 3-isochromanone is converted into a methyl 2-halomethylphenylacetate using a hydrogen halide in methanol, followed by reaction with the metal salt of a hydroxyaryl or heteroaryl compound and the subsequent transformation of the methyl acetate group into a methyl methoxyacrylate group. The transformation is said also to be accomplished in two steps if the isochromanone is treated with the hydrogen halide in a non-alcoholic solvent and the resulting phenylacetic acid esterified. In another method, when the aryl or heteroaryl group is sufficiently activated, the compounds may be prepared from a methyl 2-(2-hydroxymethylphenyl)-3-methoxyacrylate and an aryl or heteroaryl species containing a leaving group such as a halide group or a $CH_3SO_4$ anion or sulphonyloxy anion, often in the presence of a base such as sodium hydride, potassium t-butoxide or potassium carbonate.

The present invention provides a novel process for preparing methyl 2-(pyrid-2-yloxymethyl)phenylacetate intermediates for use in the production of methyl 2-[2-(pyrid-2-yloxymethyl)phenyl]-3-methoxyacrylate pesticides.

According to the present invention there is provided a process for preparing a methyl 2-(pyrid-2-yloxymethyl) phenylacetate of formula (I)[1] wherein A and D are independently H, halo, haloalkyl, haloalkoxy, phenyl, phenoxy, nitro, amino, acylamino, cyano, carboxy, alkoxycarbonyl or alkylcarbonyloxy or equivalent and m is 0 or an integer of from 1 to 3 provided that A is other than H when m is an integer of from 1 to 3, which comprises reacting a 2-pyridine of formula (II) wherein L is a leaving group and A, D and m are as defined above, with a compound MO—$CH_2$R wherein M is a metal atom and R is the residue of a metal salt of 2-phenylacetic acid, and methylating the metal salt of the 2-pyridyloxymethyl-phenylacetic acid so obtained.

Halo is typically fluorine, chlorine or bromine.

The alkyl moiety of haloalkyl, haloalkoxy, alkoxycarbonyl and alkylcarbonyloxy contains for example, from 1 to 8 or 1 to 6, typically from 1 to 4, carbon atoms in the form of straight or branched chains. Examples are methyl, ethyl, n- and iso-propyl, n-, sec, iso- and tert-butyl, n-hexyl and n-octyl.

Examples of haloalkyl groups include halo($C_{1-4}$)alkyl, typically halomethyl and haloethyl, which include trifluoromethyl, difluoromethyl, fluoromethyl, trichloromethyl, dichloromethyl, chloromethyl and pentafluoroethyl. Examples of haloalkoxy are trifluoro- and trichloromethoxy. Examples of alkoxycarbonyl and alkylcarbonyloxy are methoxycarbonyl and acetoxy. Acylamino includes, in particular, $C_{1-4}$ alkanoylamino, for example, formamido and acetylamino.

Phenyl and phenoxy groups may themselves be substituted by one or more substituents. Suitable substituents include, for example, halo, $C_{1-6}$ alkyl, halo($C_{1-4}$)alkyl, $C_{1-4}$ alkoxy, thio($C_{1-4}$)alkoxy, halo($C_{1-4}$)alkoxy, phenyl, phenoxy, cyano, nitro, amino, mono- or di-($C_{1-4}$) alkylamino, $C_{1-4}$ alkanoylamino, carboxy, $C_{1-4}$ alkoxycarbonyl or $C_{1-4}$alkylcarbonyloxy.

Where m is 2 or 3, the substituent D may have the same or different values.

The metal atom M in the compound MO—$CH_2$R and the metal in the metal salt of the residue R may be an alkali or alkaline earth metal, or it could be another metal, for example, silver. Usually, it will be sodium or potassium and M and the metal in the metal salt of the residue R will be the same. Thus the compound MO—$CH_2$R will usually be the di-sodium or di-potassium salt of 2-hydroxymethylphenylacetic acid.

The leaving group L of the pyridine of formula (II) is in the 2-position of the pyridine ring and is any suitable leaving group for ether formation with a benzyl alcohol. Examples include halide (chloride, bromide or iodide) and an alkylsulphonyl group.

Methylation of the metal salt of the 2-pyridyloxymethylphenylacetic acid is carried out with any suitable methylating agent, typically dimethyl sulphate or methyl iodide. However, other methods can be used, for example, treatment with thionyl chloride followed by the addition of methanol.

In one aspect the invention provides a process for preparing a compound of formula (I), wherein A and D are as defined above and m is 0 or 1, which comprises reacting a compound of formula (II) wherein L is halo or methylsulphonyl and A, D and m are as defined above, with a compound of formula (III) wherein M is an alkali metal, and methylating the metal salt of the 2-pyridyloxymethylphenylacetic acid so obtained.

Where m is 1, D is attached, for example, to the 4-position of the pyridine ring.

Thus, in another aspect, the invention provides a process for preparing a compound of formula (I) wherein A and D are independently halo (especially chloro or bromo) or halo-($C_{1-4}$)alkyl (especially trifluoromethyl), m is 0 or 1 and where m is 1, D is attached to the 4-position of the pyridine ring, which comprises reacting a compound of formula (II) wherein L is halo or methylsulphonyl and A and D are as defined above, with a compound of formula (III) wherein M is sodium or potassium, and methylating the 2-pyridyloxymethylphenylacetic acid so obtained.

The invention process is conveniently carried out by heating the 2-pyridine with the compound MO—$CH_2$R in a suitable solvent at elevated temperature until reaction is as complete as desired, and then adding a suitable methylating agent. A catalyst such as potassium iodide or a crown ether may be used to assist reaction.

The temperature of reaction will depend on the solvent employed but is suitably in the range of from 50° C. to 120° C., typically 60° C. to 115° C. N-Methylpyrrolidone is a suitable solvent.

The compound (I) can be isolated by drowning the reaction mixture into water and extracting it with a suitable water-immiscible solvent such as diethylether. The ether extracts can be washed with water, dried and the ether removed by evaporation.

The starting material MO—$CH_2$R, wherein M is a metal atom and R is the residue of a metal salt of 2-phenylacetic acid, is a novel compound and forms another aspect of the present invention. In particular, the invention further provides a compound of formula (III) where M is a metal atom, suitably an alkali metal or alkaline earth metal atom, for example, sodium or potassium. The disodium salt of 2-hydroxymethylphenylacetic acid is particularly mentioned.

The invention also provides a process for the preparation of the compound MO—CH$_2$R which comprises treating 3-isochromanone with a metal salt under basic conditions. In particular, it provides a process for the preparation of the compound of formula (III) wherein M is an alkali metal, which comprises treating 3-isochromanone with an alkali metal hydroxide. The process is conveniently carried out by heating 3-isochromanone at a temperature of from 40 to 130° C., for example from 50 to 110° C., typically from 50 to 85° C., for instance at around 80° C., in an aqueous, basic solution containing the metal salt together with a suitable solvent such as toluene. The product can be isolated as a solid by separating the aqueous and organic layers, adding more water, if necessary, to dissolve any precipitated product, and reducing the aqueous layer to dryness using for, example, distillation or azeotropic distillation techniques.

Conveniently, the compound (I) can be prepared from 3-isochromanone in a "one-pot" process without the intermediate isolation of the compound of formula MO—CH$_2$R. Thus in yet another aspect, the invention provides a process for the preparation of a methyl 2-(pyrid-2-yloxymethyl) phenylacetate of formula (I) wherein A and D are independently H, halo, haloalkyl, haloalkoxy, phenyl, phenoxy, nitro, amino, acylamino, cyano, carboxy, alkoxycarbonyl or alkylcarbonyloxy or equivalent and m is 0 or an integer from 1 to 3 provided that A is other than H when m is an integer of from 1 to 3, which comprises the steps:

(a) treating 3-isochromanone with a metal salt under basic conditions to form a compound MO—CH$_2$R wherein M is a metal atom and R is the residue of a metal salt of 2-phenylacetic acid, and (b) contacting the product of step (a) with a 2-pyridine of formula (II) wherein L is a leaving group and A, D and m are as defined above, and methylating the metal salt of the 2-pyridyloxymethylphenylacetic acid so obtained.

In further aspects of the present invention, steps (a) and (b) of the "one-pot" process may be refined as described previously for each of those steps individually.

Step (a) of the "one-pot" process can be carried out by heating 3-isochromanone, as described above, in an aqueous, basic solution containing the metal salt together with a solvent such as toluene or cyclohexane, which can be used to remove water, after ring opening, by azeotropic distillation. Alternatively, a different solvent such as N-methyl-pyrrolidone can be used, and toluene or cyclohexane added after ring opening to permit water removal. A phase transfer catalyst such as cetrimide or polyethylene glycol 400 dimethylether can be used to assist reaction. After distillation, the residual mixture is cooled to the appropriate reaction temperature for step (b) of the process and the 2-pyridine added. After reaction, the 2-pyridyloxymethylphenylacetic acid is methylated and the methyl ester isolated as described above.

The 2-pyridines used in the process of the invention are either already commercially available or can be prepared from commercially available materials by methods well documented in the chemical literature. 3-Isochromanone is commercially available.

The product of the invention process is a useful intermediate for the preparation of agricultural fungicides and insecticides, such as those described in EP-A-0278595. Processes for preparing these fungicides from the intermediates by formylation and methylation are fully described therein.

Examples of the methyl 2-(pyrid-2-yloxymethyl) phenylacetates (I) prepared by the process of this invention are illustrated in Table I.

TABLE 1

| Compound No. | A | D | m |
|---|---|---|---|
| 1 | Cl | — | 0 |
| 2 | Br | — | 0 |
| 3 | CF$_3$ | — | 0 |
| 4 | H | — | 0 |

The following Examples illustrate the invention. Unless otherwise stated, magnesium sulphate was used to dry solutions, solutions were concentrated under reduced pressure, reactions involving water-sensitive reagents were performed under an atmosphere of nitrogen and solvents were dried before use, where appropriate. Chromotography was performed on a column of silica gel as the stationary phase and NMR spectrum were recorded using CDCl$_3$ solutions. The following abbreviations are used throughout:

| | |
|---|---|
| TLC = thin layer chromatography | s = singlet |
| GC = gas chromatography | d = doublet |
| NMR = nuclear magnetic resonance | t = triplet |
| ppm = parts per million | m = multiplet |
| NMP = N-methylpyrrolidone | |

EXAMPLE 1

This Example illustrates the preparation of the di-sodium salt of 2-hydroxymethylphenylacetic acid.

A mixture of sodium hydroxide (0.54 g, 13.6 mmol), water (30 ml) and toluene (30 ml) were vigorously stirred and warmed to 40°0 C. 3-Isochromanone (1 g, 6.8 mmol) was added to the stirred mixture in a single portion and the reaction mixture heated to about 80° C. After 1 hour, stirring was discontinued and the organic and aqueous layers allowed to separate. TLC and GC analysis of the organic (toluene) layer showed no isochromanone present. The two layers were separated. The aqueous layer shaken with toluene (30 ml) and the toluene separated.

The aqueous layer was evaporated to dryness using fresh toluene to azeotropically distil the water and acetone to azeotropically distil off the toluene, giving a dry, free flowing pale yellow solid (1.4 g, 98.7% yield) which did not melt or decompose below 300° C.; $^1$H NMR (50:50 d$_6$mso:d$_2$o; 270 MHz) δ: 3.29(2H,s), 4.37(2H,s), 7.00–7.15 (3H.m), 7.20(1H,m) ppm.

EXAMPLE 2

This Example illustrates the preparation of methyl 2-(6-chloropyrid-2-yloxymethyl)-phenylacetate (Compound No.1 in Table I).

A mixture of the di-sodium salt of 2-hydroxymethylphenylacetic acid (1 g, 4.8 mmol, obtained as described in Example 1), 2,6dichloropyridine (1.4 g, 9.5 mmol), NMP (10 ml) and a catalytic amount of potassium iodide was stirred in pre-dried apparatus at about 95° C. overnight, giving a murky brown solution. Dimethyl sulphate (3 ml) was added to the stirred reaction mixture in one portion and the temperature maintained at 95° C. for a further 3 hours.

The reaction mixture was allowed to cool, drowned into water and the product extracted with ether. The ether extracts were washed with water, dried and the ether removed by evaporation. The crude product was purified by chromatography (eluent 1:9 ethyl acetate:hexane) to give the title product as a yellow oil (100 mg, 7% yield); $^1$H NMR (270 MHz) δ: 3.68(3H,s), 3.82(2H,s), 5.40(2H,s), 6.65(1H, d), 6.90(1H,d), 7.25–7.35(3H,m), 7.48(1H,m), 7.50(1H,t) ppm.

EXAMPLE 3

This Example illustrates the preparation of methyl 2-6-bromopyrid-2-yloxymethyl)-phenylacetate (Compound No.2 in Table I).

A mixture of the disodium salt of 2-hydroxyphenylacetic acid (1 g, 4.8 mmol, obtained as described in Example 1), 2,6dibromopyridine 0.087 g, 4.8 mmol) and NMP (10 ml) was stirred in pre-dried apparatus at 60° C. overnight, giving a murky brown solution. The reaction mixture was cooled to around 40° C. and dimethyl sulphate (3 ml) added in one portion. The resulting clear light brown solution was heated to about 60° C. and stirred for 4 hours.

The reaction mixture was allowed to cool, drowned into water and the product extracted with ether. The ether extracts were washed with water, dried and the ether removed by evaporation. The crude product was purified by chromatography (eluent 1:9 ethyl acetate:hexane) to give the title product as a yellow oil (272 mg, 17% yield); $^1$H NMR (270 MHz) δ: 3.68(3H,s), 3.84(2H,s), 5.49(2H,s), 6.68(1H, d), 7.06(1H,d), 7.25–7.35(3H,m), 7.40(1H,t), 7.49(1H,m) ppm.

EXAMPLE 4

This Example illustrates the preparation of methyl 2-(6-trifluoromethylpyrid-2-yloxymethyl)phenylacetate (Compound No.3 in Table I).

A mixture of the di-sodium salt of 2-hydroxymethylphenylacetic acid (1 g, 4.8 mmol, obtained as described in Example 1), 2-chloro-6-trifluoromethylpyridine (0.87 g, 4.8 mmol) and NMP (10 ml) was stirred in pre-dried apparatus at 60° C. overnight, giving a murky brown solution. The reaction mixture was cooled to around 40° C. and dimethyl sulphate (3 ml) added in one portion. The resulting clear light brown solution was heated to about 60° C. and stirred for 4 hours.

The reaction mixture was allowed to cool, drowned into water and the product extracted with ether. The ether extracts were washed with water, dried and the ether removed by evaporation. The crude product was purified by chromotography (eluent 1:9 ethyl acetate:hexane) to give the title product as a yellow oil (460 mg, 29% yield); $^1$H NMR (270 MHz) δ: 3.68(3H,s), 3.84(2H,s), 5.46(2H,s), 6.90(1H, d), 7.20–7.35(4H,m), 7.52(1H,m), 7.70(1H,t) ppm.

EXAMPLE 5

This Example illustrates the preparation of methyl pyrid-2-yloxymethylphenylacetate (Compound No.4 in Table I).

A mixture of the di-sodium salt of 2-hydroxymethylphenylacetic acid (0.5 g, 2.4 mmol obtained as described in Example 1), 2-methylsulphonylpyridine (0.38 g, 2.4 mmol), 15-crown-5 (1 drop) and NUT (10 ml) were stirred at around 130° C. for 5 hours. The dark brown reaction mixture was allowed to stand overnight. Methyl iodide (3 ml) was added and the reaction mixture stirred at ambient temperature for 3 hours, before drowning into water and extracting the product with ether. The ether extracts were washed with brine, dried and the ether removed by evaporation. The crude product was purified by chromatography (eluent 1:9 ethyl acetate:hexane) to give the title product as a yellow oil (95 mg, 15% yield); $^1$H NMR (270 MHz) δ: 3.66(3H,s), 3.80 (2H,s), 5.40(2H,s), 6.75(1H,dt), 6.88(1H,ddd), 7.30(1H,m), 7.48(1H,m), 7.57(1H,ddd), 8.18(1H,ddd) ppm.

EXAMPLE 6

This Example illustrates the preparation of methyl 2-(6-trifluoromethylpyrid-2-yloxymethyl)phenyl acetate (Compound No.3 in Table I) from 3-isochromanone in a "one-pot" process.

Sodium hydroxide (0.8 g, 0.02 mol) was suspended in NMP (10 ml) at room temperature. 3-Isochromanone (1.7 g, 0.01 mol) was added and the stirred mixture heated to 50° C. and held at that temperature for 1 hour. Cyclohexane (10 ml) was then added, the temperature raised and water removed by azeotropic distillation of the cyclohexane (internal head temperature 130° C.). The mixture was cooled to 65° C., 2-chloro-6-trifluoromethyl-pyridine (2.0 g, 0.011 mmol) added in one portion and the temperature held at 65° C. for about 5 hours. Dimethyl sulphate (2 ml) was added in two portions with effervescence and a rise in temperature to 100° C. The temperature was re-adjusted to 65° C. and the mixture held at that temperature for a further 30 minutes.

After standing overnight at ambient temperature, the reaction mixture was drowned into water (40 ml) and the product extracted with ether (3×50 ml). The ether extracts were washed with water, dried and the ether removed by evaporation. The crude product was extracted with n-hexane (4×25 ml) and the hexane evaporated to give a pale orange oil. Part of the oil (0.253 g) was purified by TLC (eluent 10% ethyl acetate/hexane) to give the title product (0.17 g at 97% by GLC, equivalent to an overall yield from pyridine of 34.6%); $^1$H NMR (270 MH) δ: 3.65(3H,s), 3.85(2H,s), 5.45(2H,s), 6.90(1H,d), 7.30(4H,m), 7.53(1H,m), 7.68(1H,t) ppm; M$^+$325.

EXAMPLE 7

This Example further illustrates the preparation of methyl 2-[6-trifluoromethylpyrid-2-yloxymethyl)phenylacetate (Compound No.3 in Table I).

A mixture of 3-isochromanone (2.0 g, 13.5 mmol), toluene (10 ml), water (2 ml) and sodium hydroxide (1.08 g, 27 mmol) was stirred at 80° C. for 90 minutes. Water (1 ml) was added to dissolve the precipitated sodium salt and the mixture was distilled through a Dean and Stark trap until all the water had been removed. The mixture was then distilled to dryness, after which NMP (20 ml) and 2-chloro-6-trifluoromethylpyridine (2.45 g 13.5 mmol) was added and stirred at 60° C. for 2 hours.

The reaction mixture was cooled to 45° C. and dimethylsulphate (1.7 g, 13.5 mmol) was added in one portion and stirred for an hour. Water (10 ml) was added and stirred overnight, then the reaction mixture was extracted with ether (3×30 ml). The combined extracts were dried and the ether removed to leave a yellow liquid (8.44 g).

Quantitative analysis by GC showed the liquid to contain the title product at 32.3% w/w, equivalent to a yield of 62%.

EXAMPLE 8

This Example further illustrates the preparation of methyl 2-[6trifluoromethylpyrid-2-yloxymethyl)phenylacetate (Compound No.3 in Table I) from 3-isochromanone in a "one-pot" process.

A mixture of 3-isochromanone (4.0 g, 27 mmol), toluene (130 ml), water (10 ml) and sodium hydroxide (2.2 g, 55 mmol) was heated to reflux, then the water was removed by azeotropic distillation until a still-head temperature of 110° C. had been achieved.

The reaction mixture was cooled to 60° C. and 2-chloro-6-trifluoromethylpyridine (5.0 g, 27 mmol) and polyethylene glycol 400 dimethylether (0.8 g) was added. The reaction mixture was then heated to reflux and held for 20 hours.

On cooling to 60° C., dimethylsulphate (3.8 g, 30 mmol) was added and stirred for 6 hours. Water (50 ml) was added and stirred overnight, after which the layers were separated and the aqueous layer extracted with toluene (20 ml). The combined extracts were washed and dried to give a toluene solution (66.9 g).

Quantitative analysis by GC showed the solution contained the title product at 3.73% w/w, equivalent to a yield of 28.4%.

CHEMICAL FORMULAE
(As in Description)

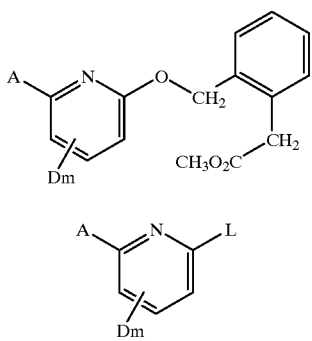

(I)

(II)

-continued

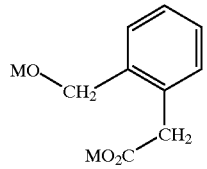

(III)

We claim:
1. A compound of formula (III):

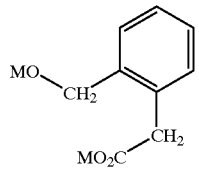

(III)

wherein M is an alkali metal or alkaline earth metal atom.

2. The disodium salt of 2 hydroxymethylphenlyacetic acid.

3. A process for the preparation of a compound of formula (III):

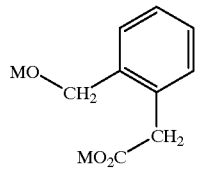

(III)

wherein M is an alkali metal, which comprises treating 3-isochromanone with an alkali metal hydroxide.

* * * * *